United States Patent [19]

Winnick

[11] 4,066,575

[45] Jan. 3, 1978

[54] PROCESS FOR THE PREPARATION OF A SUPPORTED SILVER CATALYST

[75] Inventor: Charles Nathan Winnick, Ridgewood, N.J.

[73] Assignee: Halcon International, Inc., New York, N.Y.

[21] Appl. No.: 708,460

[22] Filed: July 26, 1976

[51] Int. Cl.$^2$ .................. B01J 23/02; B01J 23/04; B01J 23/50

[52] U.S. Cl. .................................. 252/475; 252/476

[58] Field of Search ............... 252/463, 475, 476; 260/348.5 R

[56] References Cited

U.S. PATENT DOCUMENTS 2,773,844  12/1956  Carlson et al. ............... 252/476 X
3,563,913  2/1971   Krijger et al. ................ 252/463
3,878,126  4/1975   Antonelli et al. ............. 252/476 X
4,010,115  3/1977   Nielsen et al. ............... 252/463 X

*Primary Examiner*—W. J. Shine
*Attorney, Agent, or Firm*—William C. Long; David Dick; Riggs T. Stewart

[57] ABSTRACT

A supported silver catalyst, having particular utility in the production of ethylene oxide by the controlled, vapor phase, partial oxidation of ethylene employing molecular oxygen as the oxidant, is prepared by impregnation procedures. After impregnation, the catalyst is activated by thermal pyrolysis in an inert atmosphere and, subsequently, an alkali metal promoter, preferably a potassium, rubidium, and/or cesium salt is added to enhance catalyst performance.

15 Claims, No Drawings

PROCESS FOR THE PREPARATION OF A SUPPORTED SILVER CATALYST

BACKGROUND OF THE INVENTION

Modern commercial production of ethylene oxide is accomplished by the vapor phase reaction of ethylene with molecular oxygen in the presence of a silver-containing catalyst. Suitable silver-containing catalysts comprise silver, at least partially in the elemental form, in a finely divided state, distributed throughout as well as on the surface of a porous refractory support material. Because of the importance of ethylene oxide as a tonnage chemical of commerce, substantial effort has been directed toward improving the performance of the catalysts used in this process, since the performance of the catalyst has a major impact on the over-all economics of the ethylene oxide production process.

The performance of an ethylene oxide catalyst, although conventionally equated with selectivity (selectivity being defined as the molar ratio of ethylene oxide formed per mole of ethylene reacting, usually expressed as a percent of the theoretical—the theoretical maximum being 100%), involves a plurality of additional factors. A catalyst should be capable of providing high ethylene conversions per pass in order to simplify the recovery of ethylene oxide from the reactor effluent (ethylene conversion per pass being defined as the ratio of the moles of ethylene reacted within the reactor or reactors to the number of moles of ethylene contained in the reactor feed gas, computed without regard to whether the ethylene is obtained as fresh feed or from recycle streams, again usually expressed as a percent of the theoretical maximum of 100%). The catalyst, additionally, should be active, particularly at relatively low reaction temperatures, and should be long-lived since replacement of the catalyst usually mandates interruption of commercial production for catalyst replacement. Activity at low temperature is a desirable feature because the lower the reaction temperature required with a fresh charge of catalyst, the greater is the room for temperature increase to compensate for deterioration of the catalyst with time. This is particularly significant when it is realized that commercial production of ethylene oxide at reactor inlet temperatures above about 300° C. is more difficult than is such production at lower reactor inlet temperatures due, among other considerations, to a tendency for thermal decomposition of the desired ethylene oxide product. Operation at temperatures in the 200° – 300° C. region provides substantial margin for variation in reactor operating conditions, while operation above about 300° C. provides less flexibility to safely compensate for such variations.

In view of these factors, much effort has been devoted to the improvement of ethylene oxide catalysts over the years and substantial attention has been devoted to catalyst preparation procedures as well as to the development of additives which would enhance the performance of ethylene oxide catalysts. Among the additives previously disclosed as having utility in the obtaining of enhanced performance are the alkaline earth metals (see U.S. Pat. No. 3,725,307) and the alkali metals (see U.S. Pat. No. 3,563,914). The latter patent emphasizes the importance of adding the alkali metal promoter to the catalyst support prior to the deposition of the silver and clearly shows that catalysts of inferior performance are obtained when it is attempted to add an alkali metal promoter to a catalyst already containing silver.

More recent work has emphasized the efficacy of alkali metals, particularly potassium, rubidium, and cesium, as promoters for ethylene oxide catalysts. For example, U.K. Patent Specification No. 1,413,251, published Nov. 12, 1975, discloses the obtaining of catalysts of enhanced selectivity by the incorporation of from 3.5 $\times 10^{-4}$ to $3 \times 10^{-3}$ gram equivalent weights of potassium, rubidium, and/or cesium per kilogram of total catalyst, provided that these promoters are coincidentally deposited with the silver upon the support, and U.S. Pat. No. 3,962,136 makes exactly the same point with respect to coincidental deposition but teaches a broader range of alkali metal promoter to be employable. However, the temperatures required to obtain commercially satisfactory conversions with such catalysts are also high. In short, these catalysts, while selective, seem to have relatively low activity.

Another illustration of the use of alkali metals as promoters is provided in Belgian Pat. No. 821,439, granted on Apr. 24, 1975. The process of this patent, however, like that of U.S. Pat. No. 3,563,914, requires that the alkali metal be deposited upon the support prior to the deposition upon the support of the silver. Again, catalysts of good selectivity but poor activity characteristics are obtained. Additionally, it is difficult to see how the process of this Belgian patent significantly differs from the process of the U.K. patent specification discussed above since the high solubility of alkali metal compounds and the relatively low solubility of many silver compounds suggests that the alkali metal compound would be leached from the support and then redeposited thereon when, subsequently, the silver is introduced upon the support. Thus, it does not seem practicable to distinguish between the process of the Belgian patent and the process of the British patent specification, and a comparison of the selectivity-activity performance of catalysts prepared by both procedures would appear to confirm this.

Processes for producing alkali metal-containing catalysts, as set forth in the patents discussed above, present difficulties when applied to the manufacture of large batches of catalysts needed for commercial ethylene oxide production facilities. The amount of alkali metal is required to be controlled within relatively narrow limits. Such control is difficult to provide in commercial catalyst production, which usually is a batch operation. Accordingly, repeated analyses are required to ensure that the desired, critical, alkali metal content is attained. Also, techniques are required for the leaching of excess quantities of alkali metal which may be deposited, either through inadvertence or because of differences in absorbtivity between silver ion and alkali metal ion. Correspondingly, the catalyst preparation process becomes more complex and expensive than would otherwise be desirable.

Attempts to date made to overcome the drawbacks referred to above are exemplified by Belgian Pat. No. 822,857, granted June 2, 1975, but have also presented substantial difficulty. The promoter systems of this patent are extremely complex, involving combinations of up to 20 different materials. The complexities associated with the use of such promoter systems, in defined quantities, are obvious. Additionally, the catalyst preparation process of this reference requires use of alkaline solutions for impregnation of the support, which in turn mandates either the preparation of a coated, as opposed to an impregnated, catalyst or requires the use of silver-complexing agents to solubilize the silver compound if a true impregnated catalyst is desired. Coated catalysts are generally recognized today as being less satisfactory than impregnated catalysts because, among other factors, the silver in a coated catalyst would appear, in commercial use, to be somewhat more prone to separate, by abrasion or otherwise, from the support.

The terms "impregnated catalyst" and "coated catalyst" have art-recognized meanings. The former are prepared by impregnation techniques while the latter are generally prepared by mechanical mixing and/or spraying techniques; see Emmet, ed., "*Catalysis*" Vol. I, Reinhold Pub. Co., New York (1954), at pages 247–248, for general descriptions of these techniques.

SUMMARY OF THE INVENTION

It has now been found that active, selective ethylene oxide production catalysts can be produced by conventional impregnation procedures wherein the silver, after deposition upon the support in the form of a liquid containing a compound or complex of silver, is converted to metallic silver, optionally together with silver oxides by an activation procedure. This activation is carried out by heating the impregnated support in an essentially oxygen-free inert gas atmosphere. Following the inert gas activation, an effective amount of a potassium, rubidium, and/or cesium salt is deposited upon the activated material to produce finished catalyst. The addition of the alkali metal salt subsequent to the activation is hereinafter referred to as "post-deposition," and the alkali metal so added is referred to as "post-deposited." It has been found that, contrary to prior art experience with post-deposition of alkali metal, such post-deposition is entirely effective in producing active and selective catalysts provided that the activation is carried out in an inert, i.e., essentially oxygen-free, environment. Indeed, catalysts prepared by the techniques of this invention appear to be as selective as and often more active than the catalysts of the prior art, activity being measured by the ethylene conversion per pass attained at a given reaction temperature.

It is unknown why the combination of inert gas activation with post-deposition of alkali metal salts should provide enhancement of both selectivity and activity in the ethylene oxide production process. Certain physical phenomena have, however, been observed. Scanning electron microscope studies of segments of catalyst particles produced by the process of this invention indicates that the silver is present in the form of masses of very small silver particles, while standard catalyst preparation techniques appear to give agglomerates of larger silver particles. Additionally, surface area measurements (using the Brunauer, Emmet, and Teller method described at "*J. Am. Chem. Soc.*," 60, 309-16 (1938) and hereinafter referred to as the "BET" method) carried out on the catalysts of this invention indicate a substantially higher surface area for these catalysts than for standard prior art catalysts, approximately 50% higher. There are thus distinct structural differences between the catalysts prepared by the process of this invention when contrasted with the processes of the prior art, but the nature of these differences is imperfectly understood and difficult, by present techniques, to accurately quantify and describe. Accordingly, the products obtained by the process of this invention are claimed as new materials, clearly different and novel in character, but which are not definable other than by the process of their preparation.

The catalyst preparation procedure of this invention thus involves a sequence of processing steps carried out in the following order:

First, a porous refractory support is impregnated with a liquid containing a compound or complex of silver. The impregnation is carried out by immersing the support in the silver-containing liquid and maintaining the liquid and the support in contact until the solution has penetrated (i.e., has been absorbed into) the pores of the support.

Second, the impregnated support particles are separated from any remaining, non-absorbed liquid. This step of course is unnecessary if no non-absorbed liquid remains. The separation may be accomplished by any convenient technique such as, illustratively, be decantation, filtration, or centrifugation, or by any similar technique.

Third, the impregnated support particles are activated by thermally decomposing the silver compound or complex to at least one member of the group consisting of silver oxides and elemental silver, at least part of the silver being in elemental form. In other words, the entirety of the silver compound or complex may be converted to elemental silver though sometimes a mixture of silver oxides and elemental silver may be formed, but at least some of the decomposition product must be elemental silver. Critical to the process of this invention is that the decomposition occur in the presence of an essentially oxygen-free inert gas atmosphere. Inert gas atmospheres containing small concentrations of oxygen, 3 mole % or less, are, for purposes of this invention, deemed to be essentially oxygen-free inert gas atmospheres. Oxygen-rich gases, such as air, are not suitable. Reducing atmospheres, such as hydrogen or carbon monoxide, are suitable activation media but are less preferred. The nature of the inert gas, however, does not appear to be of any criticality, and suitable inert gases include nitrogen, superheated steam, carbon dioxide, the noble gases (helium, neon, argon, etc.), and low molecular weight hydrocarbons (especially $C_1$-$C_3$ paraffin hydrocarbons and $C_2$-$C_3$ olefins), and mixtures of any one or more of the foregoing. Nitrogen is a preferred inert gas activation medium.

Fourth, an effective amount of an alkali metal salt or salts is deposited upon the activated material obtained as product from the third step. Suitable alkali metals are potassium, rubidium, or cesium, or mixtures of one or more of these materials. Use of cesium is preferred over rubidium and rubidium is preferred over potassium. Effective amounts are expressed in terms of gram atoms of deposited alkali metal per kilogram of final catalyst (abbreviated as "g-at/kg") and can vary within the range of $4 \times 10^{-5}$ to $4 \times 10^{-3}$ g-at/kg. Amounts of alkali metal from $8 \times 10^{-5}$ to $1.5 \times 10^{-3}$ g-at/kg are desired and amounts of alkali metal from about $1.6 \times 10^{-4}$ to $7.5 \times 10^{-4}$ g-at/kg are preferred. The anion component of the alkali metal salt can be organic or inorganic (or mixtures of both forms) but preferably should not contain major proportions of halogen, either in free form (i.e., as the halide) or in combined form (e.g., as the oxyhalide). Alkali metal salts with anions containing sulfur (e.g., sulfides, sulfates, sulfites, thio compounds, etc.) are preferably not employed.

The four steps just described are hereinafter referred to for convenience, respectively, as (1) impregnation, (2) separation, (3) activation, and (4) post-deposition.

In addition to the steps described above, other features can, with advantage, be incorporated into the catalyst preparation process. For example, promoter metals can be deposited upon the support during the impregnation step, most conveniently by incorporating a salt of the promote or promoters in the silver-containing liquid, the salt of course being chosen to be soluble in the liquid. Preferred promoter metals for incorporation in this fashion include gold, platinum, and the alkaline earth metals as well as mixtures of two or more such materials. Calcium and barium, and especially barium, are particularly preferred additives for incorporation in this manner. When such promoters are employed, it is preferred to employ them in quantities such that the finished catalyst contains 10-5,000 parts of promoter (by weight, expressed as metal) per million parts by weight of finished catalyst (hereinafter abbreviated as "ppm"). Amounts of promoter in the range of 50 to 1,000 ppm are desired, while amounts of promoter in the range of 100 to 500 ppm are preferred. Although the promoter is added in the form of a soluble salt, it is probably converted during activation or during later use in ethylene oxide production essentially to an oxide form or to a mixture of oxide forms.

An additional step preferably employed during the catalyst preparation process is the incorporation of an oxidation step subsequent to activation but prior to post-deposition. In this step, the elemental silver-containing impregnated particles are heated in the presence of an oxygen-containing gas, preferably air, at a temperature in the range of 160° – 300° C., desirably in the range of 180° – 250° C. and preferably in the range of 200° – 230° C. This step does not supplant the activation which, as indicated, is carried out in an essentially oxygen-free inert gas atmosphere. This oxidation step appears to convert the catalyst from a somewhat hydrophobic material to a hydrophilic material and thus facilitates the post-deposition step. Without oxygen treatment, it has been found that the activated catalyst can absorb about 3-10% of its weight upon immersion in water. With the oxygen treatment, water absorption increases markedly, to a level of ca. 20% by weight or even more.

Additional activation after the post-deposition is not required. The post-deposited alkali metal is effective in the salt form without further treatment. It is suspected, however, that during use in ethylene oxide production, the alkali metal gradually undergoes conversion to the oxide and remains effective in that form.

Catalysts prepared in accordance with this invention contain 3-25% by weight of silver, expressed as metal, deposited upon the surface of and throughout the pores of a porous refractory support. Silver contents higher than 25% by weight of total catalyst are effective but result in catalysts which are unnecessarily expensive.

Silver contents, expressed as metal, of 7-20% based on weight of total catalyst are desired while silver contents, on the same basis, of 8-15% are especially preferred.

The nature of the porous refractory support is not critical to the process of this invention. Thus, this process is applicable to any of the conventional prior art supports. This is not to say that support characteristics will not influence catalyst performance; it is known that relationships between support characteristics and performance exist from, for example, U.S. Pat. No. 3,664,970. The process of this invention, however, is applicable to all conventional supports for ethylene oxide catalysts in the sense that the use of the process of this invention will produce a catalyst of enhanced performance, irrespective of support, when compared with a catalyst obtained with the same support but using prior art catalyst preparation procedures.

Catalysts of good performance are obtained with supports comprising alumina, silica, mixtures of silica and alumina, silica-alumina, and silicon carbide, whether obtained from natural sources or synthetically prepared. Preferred supports are alpha-alumina-containing materials, optionally also containing up to 15-20 wt. % of silica. Especially preferred supports have an apparent porosity of at least 30% and preferably an apparent porosity in the range of 40-60%. Preferred supports also have at least 30% and preferably at least 50% of their pores with diameters in the range of 10 to 100 microns. Preferred supports are also of low surface area. By "low surface area" is meant that the support has a surface area of less than 10 sq. meters/gram, desirably less than 1.0 sq. meter/gram, and preferably in the range of 0.005-1.0 sq. meter/gram, especially 0.01-0.10 sq. meter/gram. Surface areas are determined by the BET method. Apparent porosities are determined by the mercury porosimeter method; see Drake and Ritter, "*Ind. Eng. Chem, Anal. Ed.*," 17, 787 (1945). Pore diameter of pore diameter distributions are determined from the surface area measurements and the apparent porosity measurements using mercury porosimetry techniques. Supports having preferred characteristics are readily available from a number of commercial sources, e.g., from the Norton Company. Illustrative low surface, alpha-alumina-containing materials commercially available from the Norton Company are marketed under the designations "SA-5203," "SA-5121," "SA-5223," and "SA-5252," which have the properties listed in the following table. Similar materials of like utility are commercially available from other sources.

| Designation | SA-5203 | SA-5218 | SA-5121 | SA-5223 | SA-5252 |
|---|---|---|---|---|---|
| Alumina, wt. % | 86.9 | 86.1 | 89.4 | 87.2 | 93.1 |
| Silica, wt. % | 11.6 | 12.0 | 9.3 | 11.1 | 5.6 |
| Apparent porosity, % | 40-45 | 38-42 | 41-46 | 34-38 | 51-57 |
| % of pores with diam. in range of (in microns): | | | | | |
| 1-10 | 20 | — | 15 | 20 | 50* |
| 10-100 | 70 | 80 | 75 | 60 | 34 |
| >100 | 10 | 20 | 10 | 20 | 6 |
| Surface area, sq. meters/gm. | 0.02-0.08 | 0.005-0.04 | 0.02-0.07 | 0.02-0.06 | 0.2-0.5 |
| Pore volume, cc/gm. | 0.21 | 0.19 | 0.22 | 0.17 | 0.31 |

* 10% of pores have diameters of >1.0 micron.

For use in commercial ethylene oxide production applications, the supports are desirably formed into regularly shaped pellets, spheres, rings, etc., since regularly shaped particles generally give lower, or at least more predictable, pressure drops. Desirably, the support particles used have "equivalent diameters" in the range from 2–12 mm. and preferably in the range of 4–10 mm. "Equivalent diameter" is an art-recognized term (see U.S. Pat. No. 3,725,307) and refers to the diameter of a sphere having the same external surface (i.e., neglecting surface within the pores of the particle) to volume ratio as the support particles being employed.

By the process of this invention, irrespective of the support used, the silver is added to the support by immersion of the support into a liquid containing a compound or complex of silver, thereby enabling the silver-containing liquid to penetrate by absorption and/or capillary action into the pores of the support. A single immersion or a series of multiple immersions, with or without intermediate drying, are employable. The concentration of the compound or complex of silver in the liquid will, in large measure, dictate the silver content of the finished catalyst unless multiple impregnations are employed. To obtain catalysts having silver contents within the preferred range, suitable impregnating solutions will generally contain from 5–50 wt. % of silver, expressed as metal, but supplied as silver compounds or complexes. The exact concentrations employed, of course, will depend upon, among other factors, the desired silver content, upon the nature of the support, and upon the viscosity of the liquid. Methods of varying silver content are conventional as also are the techniques for analytical determination of the amount of silver actually deposited.

The impregnating medium is herein referred to as a liquid containing a compound or complex of silver. This is intended to encompass solutions and complexes of silver salts, both aqueous and non-aqueous, as well as molten silver salts, with or without additional diluents.

A common, suitable and readily prepared form of liquid containing a compound or complex of silver suitable for use in this invention is a molten silver salt of an organic acid, either alone or in combination with excess organic acid. The carboxylate anion associated with such silver salts is not critcial. With equal facility, one can employ monobasic, dibasic, or tribasic hydrocarbyl, aliphatic carboxylate anions, the valence requirements of which can be wholly or only partially satisfied with silver cation. Thus, for example, one may employ silver acetate, benzoate, oxalate, malonate, succinate, glutarate, and maleate. One may also employ hydroxy-substituted carboxylate anions such as, for example, the malate, lactate, citrate, glycolate, tartarate, etc., ions. Salts of hydroxy-substituted carboxylic acids and of dibasic acids are especially preferred. To enable relatively high silver levels on catalyst to be developed with a minimal number of immersions, anions containing more than 12 carbon atoms are generally not as desirable as those containing 12 carbon atoms or less. It is, however, preferred to avoid carboxylate anions containing halo and/or sulfur substituents. Accordingly, illustrative of the especially preferred silver salts would be silver acetate, silver oxalate, silver citrate, silver lactate, silver benzoate, etc. Silver complexes such as the acetylacetonate or like complexes of silver with an organic moiety are equally well employed. Aqueous solutions of inorganic silver compounds such as silver nitrate and ammoniacal silver carbonate can be employed. Such solutions preferably also contain an organic compound such as the acids mentioned above, alkyl amines such as alkyl diamines and ethanolamine, and the like.

As indicated, the silver is deposited upon the support by immersion of the support into a liquid containing a compound or complex of silver until the solution has been absorbed into the pores of the support. Time and temperature of immersion are not critical, so long as sufficient time has been allowed for the desired absorption, and are of no criticality whatsoever if multiple absorptions are contemplated. Assuming a single absorption, the amount of time required for such absorption will depend upon the form of silver used, its concentration in the liquid, and the temperature at which the solution is maintained during immersion. Typical immersion times of from 1 to 60 minutes at temperatures of from 30° to 120° C. will usually suffice to achieve silver contents of as high as 10–25 wt. %, as silver, with preferred systems wherein molten silver carboxylate salts with molten excess carboxylic acid, containing of the order of 30 to 60% silver, expressed as metal, are used. Naturally, higher temperatures are correlative with shorter contact times and vice versa.

If aqueous systems are employed, it is preferred that the immersion be conducted at temperatures (and/or pressures) such that substantial vaporization of the water does not occur, meaning that the contacting is preferably conducted at super-atmospheric pressures if immersion temperatures are to exceed 95°–100° C., while atmospheric pressure is adequate if contacting temperature is to be in the range from ambient to about 95° C.

In addition to the silver compound or complex, the liquid in which the support is immersed can advantageously contain other ingredients. For example, if an alkaline earth metal promoter is to be incorporated into the catalyst, it is advantageously incorporated in this step by adding to the liquid a salt of the promoter metal which is soluble in the liquid in an amount sufficient to provide the desired promoter metal content in the finished catalyst. The anion associated with the promoter metal is not critical and the same or similar anions as those mentioned in connection with the silver compound or complex can be employed.

Additionally, because it is desired to maintain the silver in an oxidized state during this step, additives are frequently employed. Among the commonest additives useful for this purpose is hydrogen peroxide.

Avoidance of premature silver deposition, as well as enhancement of the ability of the silver compound or complex to permeate the support, is provided if the silver salt solution is maintained in an acid state, preferably by incorporation of free carboxylic acid, preferably that corresponding to the anion of the silver salt. Such liquids are readily made, for example, by admixing silver oxide with a carboxylic acid such as lactic acid and heating and causing the oxide to react with the acid to form the silver carboxylate, dissolved in excess carboxylic acid, liberating by-product water which need not be removed from the liquid.

Following such a procedure, and assuming that it is desired to employ silver lactate as the silver salt and to incorporate barium (supplied as barium acetate) as a promoter, a typically suitable liquid, after reaction of the silver oxide with lactic acid, would contain:

| Component | Wt. % |
| --- | --- |
| Silver lactate | From 55 to 73 |
| Lactic acid | From 15 to 45 |
| Barium acetate | From 0.05 to 0.30 |

-continued

| Component | Wt. % |
|---|---|
| Hydrogen peroxide (100% basis) | From 0 to 0.5 |
| Water | From 0 to 20 |

The hydrogen peroxide would have been added, as indicated above, to maintain the silver in an oxidized state.

Liquids of the concentrations set forth above will readily provide finished catalysts having silver contents, expressed as metal, of from 8% to 15% based on weight of total catalyst and barium contents within the preferred range of from 100 to 500 ppm, with but a single immersion step.

Following impregnation, the support is separated from any non-absorbed solution. The method for accomplishing this separation is of no criticality and any convenient technique can be used including, illustratively, decantation, filtration, or centrifugation. If the immersion is carried out by the simple technique of placing the support in a perforated container and lowering the container into a vessel containing the solution, the separation is readily accomplished by merely withdrawing the container from the vessel and allowing surplus solution to drain freely for 3 to 5 minutes or longer.

The catalyst is then activated by heating the impregnated particles to a sufficient temperature to decompose the silver compound or complex, at least in part, to elemental silver in an essentially oxygen-free inert gas atmosphere. Desirably, the dried particles are gradually heated to a temperature in the range of about 300° to 400° C. or even higher and held at this temperature for a sufficient time to complete the activation. At ca. 350° C. this is readily accomplished in from 0.2 to 3.0 hours. An essentially oxygen-free inert gas atmosphere must be present during this step. Preferably, a stream of inert gas is passed through the catalyst particles at a rate of at least 0.0015 normal cubic meters (gas volume measured at 0° C. and 760 mmHg) per hour per kilogram of particles (abbreviated as "$NM^3$/hr-kg") to facilitate removal of volatile decomposition products from the particles during activation. The inert gas may be employed on a once-through basis or may be recirculated in whole or in part, whichever is most convenient.

At this point in the catalyst preparation procedure, the silver compound or complex has been converted to elemental silver, perhaps together with one or more of the silver oxides. However, as has been pointed out above, the catalyst is distinctly hydrophobic. Accordingly, as a preferred option, the catalyst is treated with oxygen at elevated temperatures to remove any residual organic material that might be contained on or within the catalyst particles. This is preferably carried out by heating the catalyst particles in an oxygen-containing atmosphere (e.g., air, although oxygen-enriched air or diluted air are also suitable) at a temperature in the range of 160°–300° C. for a period of from 0.5 to 24 hours. In this step, if employed, it is preferred to use temperatures in the range of 200°–230° C. since the prolonged use of temperatures higher than about 250° C. tends to somewhat decrease the selectivity of the finished catalyst, perhaps because of agglomeration of finely divided silver particles. Assuming air is used, it is preferred to pass an air stream through the catalyst with the air flow rate being adjusted to control temperature to the desired level. An air flow rate of 0.005–0.5 $NM^3$/hr-kg or more is generally employed.

The final step in the catalyst preparation process of this invention requires the post-deposition of an alkali metal salt such that the final catalyst contains from $4 \times 10^{-5}$ to $4 \times 10^{-3}$ g-at/kg of the alkali metal. The post-deposition can readily be accomplished by a procedure analogous to that used for the silver deposition, i.e., immersion of the activated catalyst particles into a solution, preferably aqueous, of an alkali metal salt, which is then followed by a separation step. The alkali metal-containing catalyst is then dried to remove adsorbed solvent under conditions which do not appear to be critical, temperatures of 80°–250° C. or more and times of 0.5–24 hours or more being entirely suitable. Alternatively, the catalyst may be immersed in an alkali metal-containing solution and maintained in contact with the solution under the influence of heat until the solvent is evaporated. Of the two methods described, the former is preferred. The latter, however, is entirely effective and, should the latter method be selected, advantage would result from the use of a non-aqueous solvent such as, for example, a lower alkanol (e.g., methanol, ethanol, propanol, isopropanol, etc.), because the lower alkanols are more easily volatilized than water at lower temperatures.

Also as indicated above, the alkali metal is post-deposited upon the support in the form of a salt. The anion associated with this salt can be organic or inorganic but preferably would not contain halogen, and also preferably would not contain sulfur. Suitable alkali metal salts encompass the carboxylate salts mentioned above in connection with the silver salt, e.g., the acetate, benzoate, lactate, and oxalate salts, but would also include, illustratively, the carbonate, bicarbonate, cyanide, nitrate, nitrite, oxide, and hydroxide salts as well.

Catalysts prepared by the procedures described above are particularly suitable for use in the production of ethylene oxide by the vapor phase oxidation of ethylene with molecular oxygen. Oxidation reaction conditions such as those previously known in the art can be employed with these catalysts. These conditions usually involve reaction temperatures of about 150°–400° C., usually 200°–300° C., and reaction pressures in the range of from 1.5–35 kg/cm²abs. Reactant feed mixtures usually contain 0.5–20% ethylene, 3–15% oxygen, with the balance comprising comparatively inert materials including such substances as nitrogen, carbon dioxide, methane, ethane, argon, and the like. Recycle operations are conventionally used in which only a portion of the ethylene is reacted per pass. After separation of the desired ethylene oxide product and the removal of appropriate purge streams and carbon dioxide to prevent uncontrolled build-up of inerts and/or by-products, unreacted materials are returned to the oxidation reaction systems.

EXAMPLES

The following examples are presented to further illustrate the present invention. Except where otherwise indicated, for liquids and solids all parts and percents are by weight; for gases, compositions are expressed in terms of mole % and flow rates are expressed in terms of normal cubic meters per hour (i.e., gas volumes measured at 0° C. and 760 mmHg and abbreviated as "$NM^3$/hr").

EXAMPLE I

Part a

Preparation of catalyst

To 3.30 parts of water are added 60 parts of 88 wt. % lactic acid, the remaining 12% of the lactic acid being water. The mixture is then heated to 85° – 95° C. and, while stirring, to this mixture are slowly added 35 parts of silver oxide. Following addition of the silver oxide, the slightly cloudy solution is stirred for an additional 30 minutes and 0.12 part of 30 wt. % hydrogen peroxide in water solution is slowly added to obtain a clear yellow solution of silver lactate in aqueous lactic acid. The resulting solution is analyzed and found to contain 37.2 wt. % silver expressed as metal.

A solution of barium acetate is prepared by admixing 12.1 parts of barium acetate and 50 parts of water and stirring until a clear solution is obtained. A portion of the resulting solution (0.6 part) is then added to the silver lactate solution.

The silver lactate-barium acetate solution is then heated to 85° – 95° C. and a perforated basket containing 60 parts of Norton SA-5121 catalyst support (having the composition and physical properties set forth in the above table) in the form of 4.76 mm spheres preheated to 110° C. is lowered into the solution. After 30 minutes at 85° – 95° C., the basket is removed and allowed to drain for 10 minutes to separate the impregnated particles from the remainder of the aqueous silver lactate solution.

A portion of the thus impregnated particles is then transferred to a steel container having a perforated screen of sufficient fineness to retain the particles at the bottom of the container. The container is then covered with a lid having means for permitting vapors to escape from the container; the covered container, containing the particles, is purged with nitrogen and placed in an oven.

Part b

Inert gas activation

Then, without removal of the particles from the container or the container from the oven, temperature is increased gradually to 350° C. and maintained at 350° C. for 1.5 hours with nitrogen flow maintained at 0.1 $NM^3hr$-kg. The now-activated catalyst is removed from the oven and allowed to cool.

Next, the catalyst is placed in a forced circulation oven and treated in an air atmosphere for 12 hours at 200° C.

Part c

Post-deposition

A solution of cesium acetate in water is prepared containing 293 ppm (weight basis) of cesium, as metal. To 45 parts of this solution are added 32 parts of the material obtained as product from part (b) above. After 30 minutes at 30° C., the catalyst is separated from the remaining solution and dried in an air atmosphere at 130° C. for 3 hours.

Analysis of the finished catalyst shows it to contain 13.4 wt. % silver, 270 ppm of barium, and 53 ppm of cesium. This cesium content is approximately equivalent to $4 \times 10^{-4}$ g-at/kg.

Part d

Catalyst testing

An oil-jacketed reactor tube having an inner diameter of 21.8 mm is charged with 2,900 grams of the catalyst prepared as described above, such that the height of the catalyst bed is about 7.3 meters. By means of the hot oil, the temperature of the bed is raised to 240° C. and a gas containing 15% ethylene, 7% oxygen, 4% carbon dioxide, and 0.1% ethane, the balance being nitrogen, is introduced to the reactor together with a small amount of ethylene dichloride (ca. 0.25 moles per million moles of total gas) at a rate of 6000 $NM^3$/hr-kg of catalyst. Temperature is maintained at 240° C. and pressure is maintained at 22.1 $kg/cm^2$ (abs.). Results observed are an ethylene conversion per pass of ca. 14%, a selectivity of 77.6%, and an ethylene oxide concentration in the outlet gas from the reactor of 1.60 mole %.

EXAMPLE II (for comparative, not illustrative, purposes)

A second portion of the impregnated particles of Example I is dried and activated as shown in Example I, but no post-deposition of alkali metal is conducted. The resultant catalyst contains 13.4 wt. % silver, as metal, 270 ppm of barium, and has no detectable cesium content. Upon testing of this catalyst at 234° C. as described in Example I, an ethylene conversion per pass of ca. 14%, a selectivity of 75.3%, and an ethylene oxide content of 1.60% in the reactor outlet gas are observed. This catalyst, when tested at the same productivity level as that employed in Example I, is thus found to be significantly less selective.

In the tables describing the remaining examples, the term "E.O.%" refers to the ethylene oxide content in the reactor outlet gas and "Sel. %" refers to the selectivity of the catalyst for the formation of ethylene oxide.

EXAMPLE III

A series of catalysts of varying cesium content are prepared with the support and according to the procedure of Example I. These catalysts are tested as described in Example I. Catalyst composition and test results obtained are:

| Run | Ag, wt. % | Ba Content, ppm | Cs Content g-at/kg | ppm | T° C | E.O. % | Sel. % |
|---|---|---|---|---|---|---|---|
| 3A | 13.2 | 264 | $7.7 \times 10^{-4}$ | 102 | 239 | 1.6 | 77.5 |
| 3B | 13.4 | 270 | $3.9 \times 10^{-4}$ | 52 | 240 | 1.6 | 77.6 |
| 3C | 12.9 | 260 | $1.8 \times 10^{-4}$ | 24 | 233 | 1.6 | 76.9 |

EXAMPLE IV

A series of catalysts of varying barium content are prepared as described in Example I, employing the same support as used in Example I. The catalysts so prepared have the following composition and when tested as described in Example I the following results are obtained:

| Run | Ag, wt. % | Ba Content, ppm | Cs Content g-at/kg | ppm | T° C | E.O.% | Sel. % |
|---|---|---|---|---|---|---|---|
| 4A | 13.6 | 544 | $3.9 \times 10^{-4}$ | 52 | 231 | 1.6 | 76.3 |
| 4B | 13.2 | 528 | $7.3 \times 10^{-4}$ | 97 | 247 | 1.6 | 76.6 |
| 4C | 13.1 | 131 | $1.7 \times 10^{-4}$ | 23 | 234 | 1.6 | 77.6 |

EXAMPLE V

The following catalysts are prepared according to the procedure of Example I but employing different catalyst supports. They are tested in a reactor with an I.D. of 12.7 mm with a 45.7 cm bed of catalyst at 22 kgcm² abs., 3000 Hr⁻¹ SV, with a gas mixture consisting of 6% oxygen, 5% ethylene, 3% carbon dioxide, 0.2 ppm of ethylene dichloride and the balance nitrogen. Catalyst compositions and test results are:

| Run | Support Designation* | Ag, wt. % | Ba Content, ppm | Cs Content g-at/kg | ppm | T° C | E.O. % | Sel. % |
|---|---|---|---|---|---|---|---|---|
| 5A | SA5218 | 14.0 | 280 | — | 0 | 225 | 1.0 | 72 |
| 5B | SA5218 | 14.0 | 280 | $3.4 \times 10^{-4}$ | 45 | 231 | 1.0 | 78 |
| 5C | SA5223 | 12.1 | 270 | — | 0 | 228 | 1.0 | 73 |
| 5D | SA5223 | 12.1 | 270 | $3.5 \times 10^{-4}$ | 47 | 232 | 1.0 | 77 |
| 5E | SA5252 | 13.6 | 290 | — | 0 | 216 | 1.0 | 70 |
| 5F | SA5252 | 13.6 | 290 | $3.3 \times 10^{-4}$ | 44 | 223 | 1.0 | 75 |

*Supplied by the Norton Company. Properties are as set forth, in tabular form, above.
Note that Runs 5A, 5C, and 5E are controls, not illustrative of the invention.

EXAMPLE VI

A series of catalysts are prepared using the procedure and support of Example I but utilizing different alkali metal promoters. The test procedure employed is that of Example V. Catalyst compositions and test results obtained are:

| Run | Ag, wt. % | Ba Content, ppm | Alkali Metal | g-at/kg | ppm | E.O. % | Sel. % |
|---|---|---|---|---|---|---|---|
| 6A | 13.6 | 280 | Cs | $3.4 \times 10^{-4}$ | 45 | 1.0 | 78 |
| 6B | 13.6 | 280 | Rb | $3.4 \times 10^{-4}$ | 29 | 1.0 | 76 |
| 6C | 13.6 | 280 | K  | $3.6 \times 10^{-4}$ | 14 | 1.0 | 73 |
| 6D | 13.6 | 280 | —  | — | — | 1.0 | 71 |

Note that Run 6D is a control, not illustrative of the invention.

EXAMPLE VII

Catalyst "A" is prepared as described in Example I but is activated in an air atmosphere at 350° C. and contains no post-deposited alkali metal. Catalyst "B" is prepared by impregnation of catalyst "A" with a cesium acetate solution, i.e., contains post-deposited alkali metal. Catalyst "C" is prepared in a fashion identical to Example I. For each, the support used in Example I is again employed. The catalysts are each tested as described in Example I and the results are:

| Run | Ag, wt. % | Ba Content, ppm | Cs Content g-at/kg | ppm | T° C | E.O. % | Sel. % |
|---|---|---|---|---|---|---|---|
| 7A | 15 | 1000 | 0 | 0 | 240 | 1.6 | 73.5 |
| 7B | 15 | 1000 | $4 \times 10^{-4}$ | 53 | 247 | 1.6 | 73.7 |
| 7C | 15 | 1000 | $3.8 \times 10^{-4}$ | 50 | 234 | 1.6 | 77.1 |

Note that Runs 7A and 7B are controls, not illustrative of the invention.

EXAMPLE VIII

A series of catalysts are prepared using the procedure and support of Example I; however, the activation is accomplished with different inert gases but otherwise at the same flow rate and approximate temperature as in Example I. They are tested as in Example I with the following results:

| Run | Gas Used | T° C | E.O. % | Sel. % |
|---|---|---|---|---|
| 8A | $CO_2$ | 243 | 1.6 | 77.4 |
| 8B | Steam | 240 | 1.6 | 77.7 |
| 8C | $CH_4$ | 238 | 1.6 | 77.5 |

EXAMPLE IX-A

To 100 parts of catalyst prepared as in Example I, parts (a) and (b), are added a solution of 0.0072 parts of cesium acetate in 30 parts of water. The mixture is then placed in a rotary evaporator which is heated to remove water and prepare a catalyst containing 50 ppm cesium.

EXAMPLE IX-B

The procedure of part A of this Example is repeated except than methanol is employed as a solvent in place of water. Catalysts "A" and "B" are then tested as described in Example I, with the following results:

| Run | Ag, wt. % | Ba Content, ppm | Cs Content g-at/kg | Cs Content ppm | T° C | E.O. % | Sel. % |
|---|---|---|---|---|---|---|---|
| 9A | 13.4 | 270 | 4 × 10⁻⁴ | 53 | 240 | 1.6 | 77.4 |
| 9B | 13.4 | 270 | 4 × 10⁻⁴ | 53 | 241 | 1.6 | 77.7 |

EXAMPLE X

Example I is repeated except that the silver lactate solution is diluted with lactic acid to produce a solution containing 30% silver. Barium acetate is added in amounts sufficient to give 450 ppm of barium in the solution. The catalyst so produced has 10.2% silver, 150 ppm barium and $3.91 \times 10^{-4}$ g-at/kg (52 ppm) of cesium. When tested as described in Example I, part (d), the following results are obtained:

| T° C | E.O. % | Sel. % |
|---|---|---|
| 244 | 1.6 | 76.5 |

What is claimed is:

1. A process for the preparation of a supported silver catalyst suitable for the production of ethylene oxide by the controlled, vapor phase, partial oxidation of ethylene with molecular oxygen, said catalyst preparation process comprising the following steps:
   a. impregnating a porous refractory support with a liquid containing a compound or complex of silver by immersing said support in said liquid and maintaining the support and the liquid in contact until the liquid has been absorbed into the pores of the support;
   b. separating the thus-impregnated particles from any non-absorbed remainder of said liquid;
   c. activating the thus-impregnated particles by converting the silver compounds or complex to at least one member of the group consisting of silver oxides and elemental silver, at least part of the silver being in elemental form, said conversion being accomplished by heating the impregnated particles in the presence of an essentially oxygen-free inert gas to a temperature at which the silver compound or complex decomposes to yield, at least in part, elemental silver;
   d. heating the activated particles in the presence of an oxygen-containing gas at a temperature in the range of 160° – 300° C. for a period of from 0.5 to 24 hours prior to step (e) hereinafter described;
   e. depositing upon the activated particles from $4 \times 10^{-5}$ to $4 \times 10^{-3}$ gram atoms per kilogram of catalyst of at least one alkali metal of the group consisting of potassium, rubidium, and cesium, said alkali metal being in the form of a salt in solution in a solvent;
   f. removing the solvent employed in step (e).

2. A process in accordance with claim 1 wherein the liquid employed in step (a) of claim 1 comprises an alkaline earth metal salt soluble in said liquid.

3. A process in accordance with claim 2 wherein the alkaline earth metal salt is a barium salt.

4. A process in accordance with claim 2 wherein the concentration of the alkaline earth metal salt is such as to provide 10-5,000 parts of alkaline earth metal salt by weight, expressed as metal, per million parts by weight of finished catalyst.

5. A process in accordance with claim 4 wherein the concentration of the alkaline earth metal salt is such as to provide 50-1,000 parts of alkaline earth metal salt by weight, expressed as metal, per million parts by weight of finished catalyst.

6. A process in accordance with claim 4 wherein the concentration of the alkaline earth metal salt is such as to provide 100-500 parts of alkaline earth metal salt by weight, expressed as metal, per million parts by weight of finished catalyst.

7. A process in accordance with claim 6 wherein the alkaline earth metal is barium.

8. A process in accordance with claim 1 wherein the temperature of treatment with the oxygen-containing gas is in the range of 180° 250° C.

9. A process in accordance with claim 1 wherein the temperature of treatment with the oxygen-containing gas is in the range of 200° – 230° C.

10. A process in accordance with claim 1 wherein the amount of alkali metal deposited upon the activated particles is from $8 \times 10^{-5}$ to $1.5 \times 10^{-3}$ gram atoms per kilogram of catalyst.

11. A process in accordance with claim 1 wherein the amount of alkali metal deposited upon the activated particles is from $1.6 \times 10^{-4}$ to $7.5 \times 10^{-4}$ gram atoms per kilogram of catalyst.

12. A process in accordance with claim 11 wherein the alkali metal is cesium.

13. A process in accordance with claim 11 wherein the alkaline earth metal is barium.

14. A process in accordance with claim 11 wherein the alkali metal is cesium and the alkaline earth metal is barium.

15. A process in accordance with claim 1 wherein the alkaline earth metal is barium and the liquid used for impregnation comprises 55-73 wt. %. silver lactate, 15-45 wt. % lactic acid, 0.05-0.30 wt. % barium acetate, 0-0.5 wt. % hydrogen peroxide, and 0-20 wt. % water.

* * * * *

UNITED STATES PATENT AND TRADEMARK OFFICE
CERTIFICATE OF CORRECTION

PATENT NO. : 4,066,575
DATED : Jan. 3, 1978
INVENTOR(S) : Charles N. Winnick

It is certified that error appears in the above-identified patent and that said Letters Patent are hereby corrected as shown below:

Col. 4, line 17 : "be" should be -- by --

Col. 5, line 6 : "promote" should be -- promoter --

Col. 6, line 14 : "catalysts" should be -- catalysis --

Col. 6, line 39 : "of" should be -- and --

Col. 6, line 47 : insert -- SA-5218 -- between "SA-5203" and "SA-5121"

Col. 14, line 57: "than" should be -- that --

Signed and Sealed this

Fifteenth Day of August 1978

[SEAL]

Attest:

RUTH C. MASON
Attesting Officer

DONALD W. BANNER
Commissioner of Patents and Trademarks